United States Patent [19]
Wolcott

[11] Patent Number: 5,469,917
[45] Date of Patent: Nov. 28, 1995

[54] USE OF CAPILLARY-MEMBRANE SAMPLING DEVICE TO MONITOR OIL-DRILLING MUDS

[76] Inventor: Duane K. Wolcott, 3406 Morning Glory Dr., Baton Rouge, La. 70808

[21] Appl. No.: 355,493

[22] Filed: Dec. 14, 1994

[51] Int. Cl.$^6$ .................................................. E21B 47/00
[52] U.S. Cl. .................. 166/250.01; 166/264; 175/60; 73/23.36; 73/23.41; 73/23.42
[58] Field of Search .................... 166/250, 264; 175/59, 60; 73/23.35, 23.26, 23.38, 23.41, 23.42

[56] References Cited

U.S. PATENT DOCUMENTS

| | | | |
|---|---|---|---|
| 3,236,092 | 2/1966 | Carter | 73/23.35 X |
| 3,398,505 | 8/1968 | Llewellyn | 73/23.35 X |
| 3,429,105 | 2/1969 | Llewellyn et al. | 73/23.35 X |
| 3,462,761 | 8/1969 | Horeth et al. | 73/23.38 X |
| 3,772,909 | 11/1973 | Anderson | 73/23.35 X |
| 3,976,450 | 8/1976 | Marcote et al. | 55/158 |
| 4,257,266 | 3/1981 | Apple | 73/155 |
| 4,266,277 | 5/1981 | Issenmann | 73/23.1 X |
| 4,319,482 | 3/1982 | Bunner | 73/153 |
| 4,353,803 | 10/1982 | Dover, Jr. | 210/728 |
| 4,479,204 | 10/1984 | Silverman | 367/47 |
| 4,492,862 | 1/1985 | Grynberg et al. | 250/255 |
| 4,833,915 | 5/1989 | Radd et al. | 73/153 |
| 4,854,322 | 8/1989 | Ash et al. | 128/635 |
| 4,887,464 | 12/1989 | Tannenbaum et al. | 73/153 |
| 4,892,383 | 1/1990 | Klainer et al. | 350/96.29 |
| 5,094,819 | 3/1992 | Yager et al. | 422/82.07 |
| 5,221,477 | 6/1993 | Melcher et al. | 210/634 |
| 5,244,810 | 9/1993 | Gottlieb | 436/68 |
| 5,317,932 | 6/1994 | Westlake, III et al. | 73/864.73 |

OTHER PUBLICATIONS

PCT International Application WO93/16790 published 2 Sep. 1993.

Primary Examiner—Roger J. Schoeppel
Attorney, Agent, or Firm—Reginald F. Roberts, Jr.

[57] ABSTRACT

A method for monitoring oil-drilling mud. A supported capillary membrane (SCMS) device having a support member, a capillary membrane permeable to hydrocarbons, and flights on the surface of the support member within which the capillary member is supported is disposed in a stream returning mud from a drill hole to the surface of an oil well. A stream of inert gas is passed through the SCMS device, thereby entraining hydrocarbon vapors in the gas stream and providing a sample of the hydrocarbons associated with the oil-drilling mud. The hydrocarbon-laden gas stream is input to an analytical instrument such as a gas chromatograph capable of identifying and quantitatively determining the concentrations of the hydrocarbons.

7 Claims, 4 Drawing Sheets

5,469,917

USE OF CAPILLARY-MEMBRANE SAMPLING DEVICE TO MONITOR OIL-DRILLING MUDS

BACKGROUND OF THE INVENTION

The present invention relates to oil drilling. More particularly, the present invention relates to the monitoring of oil-drilling muds.

In drilling for oil, one of the most important operations is monitoring the drilling "mud" circulated down the well bore and returned to the surface. This mud transports drill cuttings to the surface to keep the well bore open, but of almost as great a level of importance is the information gained about conditions "down-hole" by monitoring various physical and chemical changes that occur as the mud traverses the well bore.

Of particular interest is the fact that the circulating mud incorporates hydrocarbons from the surrounding rock as the drill bit passes. Accurate knowledge about the types and quantities of hydrocarbons revealed as the drill bit penetrates different rock strata is critical to determining how to "bring in" the well as an operating production unit. This operation of determining the hydrocarbon content of the returned mud is one of the more important operations of mud logging. As currently practiced and as taught by the prior art, a sample of gas is extracted from the drilling mud at ground level, using a gas trap. The trap is a metal box immersed in the shale-shaker ditch. Ports in the lower part of the trap allow mud to enter and leave the trap. An agitator motor provides pumping and degassing of mud passing through the trap. The development of a continuous gas trap with good and consistent efficiency has been a high priority in the improvement of mud-logging technology. As presently practiced, the extraction of gas samples from the mud comprises bubbling an extractant gas directly through the mud slurry, then separating the gas from the slurry and cleaning the gas for inputting to the analytical instruments used for hydrocarbon detection, identification, and quantitative determination.

The supported capillary-membrane sampling (SCMS) device is an apparatus characterized by a grooved support member having a tubular membrane, capillary column, or the like supported within the groove of the support member. This apparatus is broadly useful for analytical and/or fluid-separation purposes. Utilization of SCMS technology would allow the elimination of the entire sample extraction—cleanup train. The present invention comprises the use of such technology in monitoring oil-drilling muds.

SUMMARY OF THE INVENTION

In general, the present invention in a first aspect provides a method for monitoring oil-drilling muds. The method comprises (a) providing a device comprising a support member, a capillary membrane permeable to hydrocarbons, and flights on the surface of the support member within which the capillary member is supported; (b) disposing the device in a stream returning mud from a drill hole to the surface of an oil well; (c) passing a stream of inert gas through the capillary membrane, thereby entraining hydrocarbon vapors in the gas stream; and (d) inputting the gas stream containing the entrained hydrocarbon vapors to an analytical instrument capable of identifying and quantitatively determining the concentration of the hydrocarbons.

In a second aspect the invention provides a method for sampling hydrocarbons associated with oil-drilling mud. The method comprises (a) providing a device comprising a support member, a capillary membrane permeable to hydrocarbons, and flights on the surface of the support member within which the capillary member is supported; (b) disposing the device in a stream returning mud from a drill hole to the surface of an oil well; and (c) passing a stream of inert gas through the capillary membrane, thereby entraining hydrocarbon vapors in the gas stream and obtaining a sample of the hydrocarbons associated with the oil-drilling mud.

DETAILED DESCRIPTION OF THE INVENTION

Figure 1:
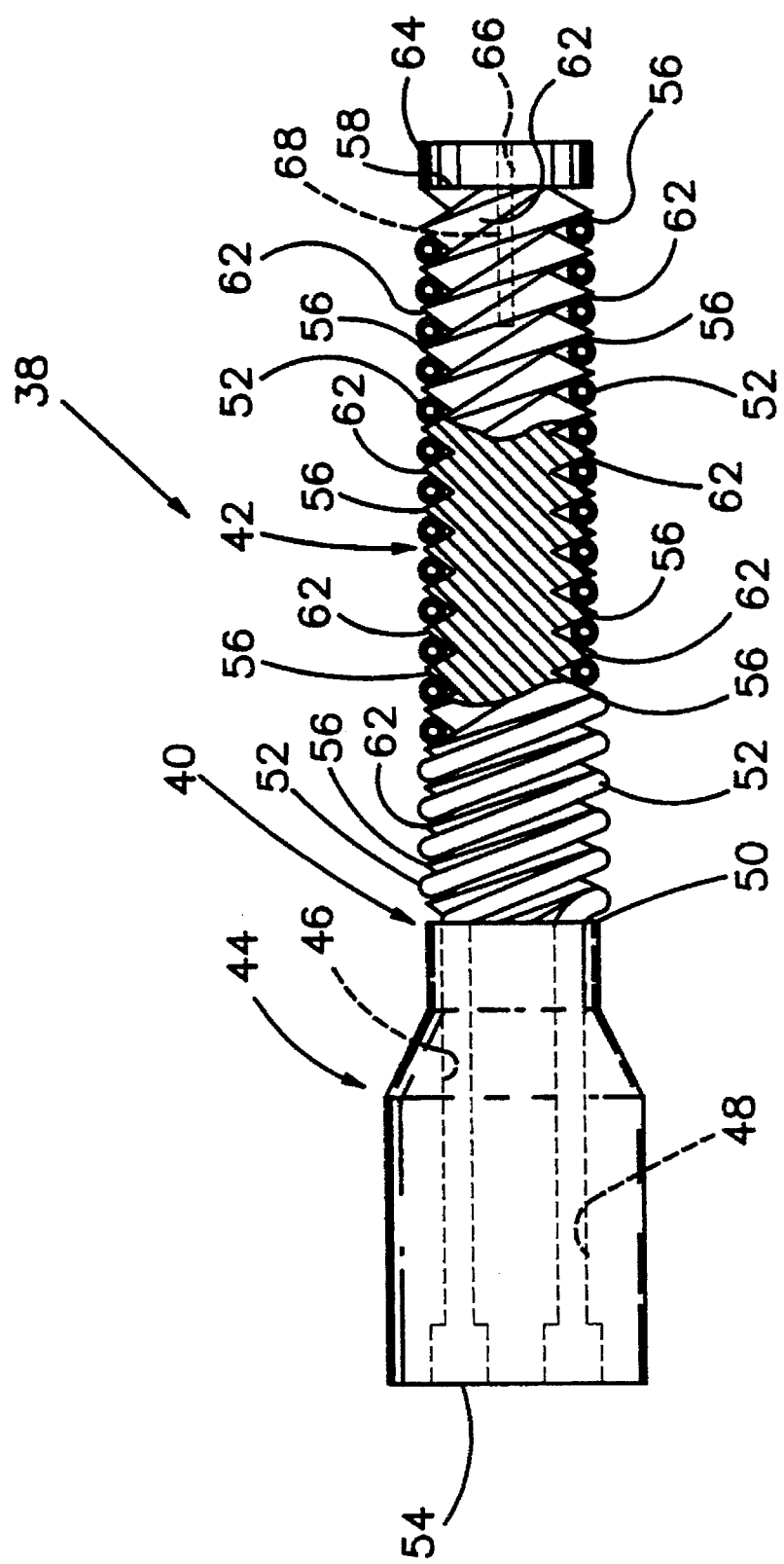
FIG. 1 is a cross-sectional view of an SCMS device.

More specifically, reference is made to FIG. 1, in which is shown an SCMS device, generally designated by the numeral 38.

The device 38 comprises a support member 40 having first and second ends 58 and 54, threaded and unthreaded portions 42 and 44, and flights 56 and 62 within which a capillary membrane 52 is supported by the support member 40. Two channels, 46 and 48, are defined longitudinally through the unthreaded portion 44 of the support member 40. The ends of the capilary membrane 52 are disposed in the channels 46 and 48.

A complete description of the SCMS device 38 is provided by Int. Pat. App. WO 93/16790 and U.S. Pat. No. 5,317,932, which are hereby incorporated by reference.

Figure 2:
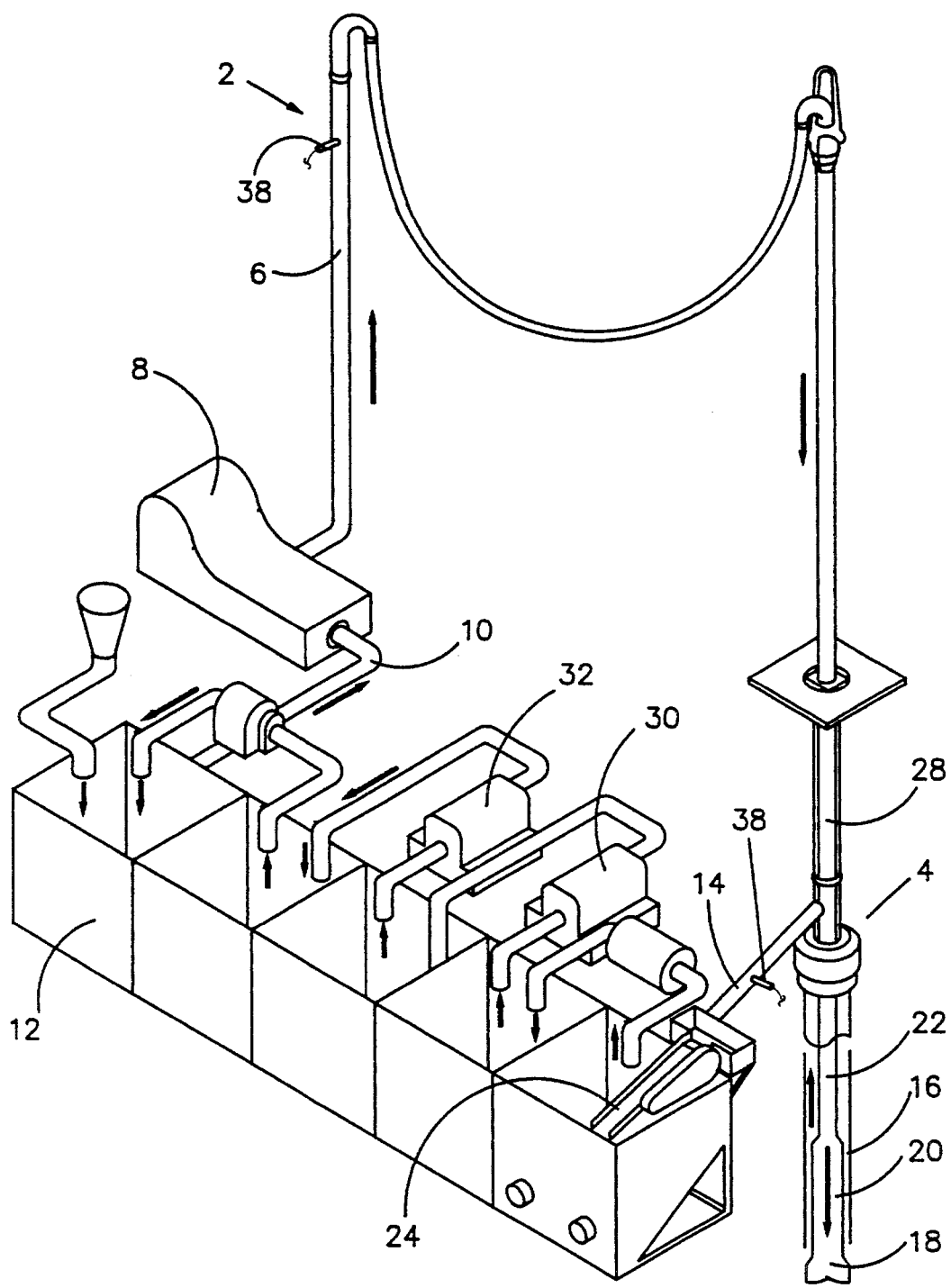
FIG. 2 is a schematic representation of a first embodiment of a method for monitoring oil-drilling mud in accordance with the principles of the present invention.

Reference is now made to FIG. 2, in which are illustrated a first embodiment, generally designated by the numeral 2, of a method for monitoring oil-drilling mud.

In the first embodiment 2 of the present invention, a first SCMS device 38 is disposed in a standpipe 6 carrying discharge from a pump 8 connected to a suction line 10 leading from a suction pit 12. A second SCMS device 38 is inserted in a mud-return flow line 14 in which mud slurry from a bore hole 16 is returned past a drill bit 18, drill collar 20, and drill pipe 22.

After passing through the mud-return flow line 14, the slurry passes through a shale shaker 24 into a settling pit 26. From the settling pit 26 the slurry passes through a degasser 28, desander 30, and desilter 32 into the suction pit 12.

The SCMS devices 38 are immersed in the pump-discharge and mud-return streams, and a stream of inert gas such as nitrogen is passed through the capillary membranes 52 by way of the channels 46 and 48. The membranes 52 are permeable to hydrocarbons. As the hydrocarbons permeate the walls of the capillary membranes 52 and enter the interior channels of the membranes, the hydrocarbon vapors are transported through the membranes 52 by the streams of inert gases. The hydrocarbon-laden gas streams exit the membranes 52 and SCMS devices 38 through the channels 46 and 48. If the channels 46 are used to input the streams of carrier gas, the channels 46 are used to output the streams of hydrocarbon-laden gas. If the channels 48 are used to input the streams of carrier gas, the channels 46 are used to output the streams of hydrocarbon-laden gas. The streams of hydrocarbon-laden gas are input to analytical instruments such as a gas chromatograph (not shown), for the identification and quantitative determination of the entrained hydrocarbons.

Figure 3:
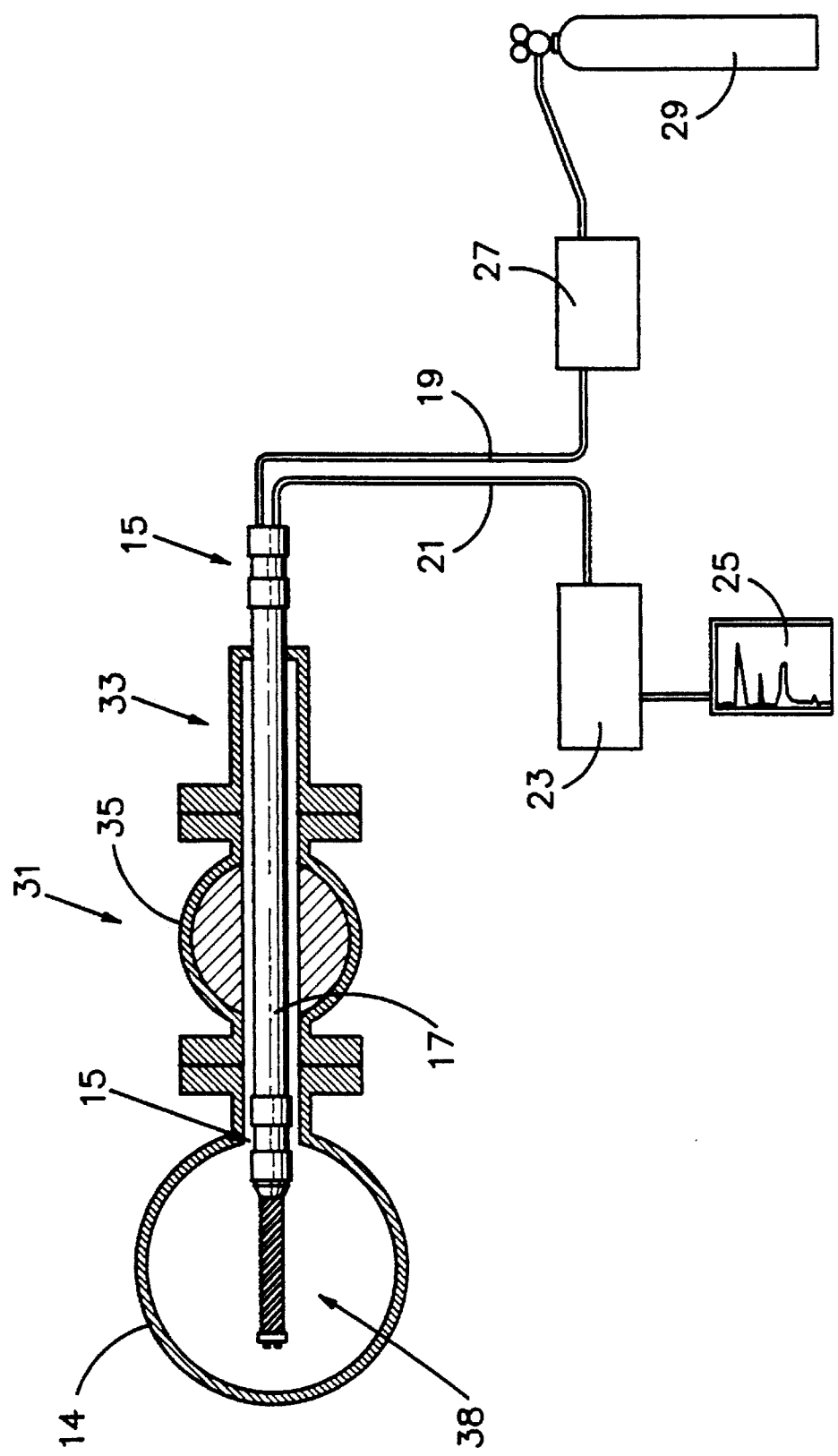
FIG. 3 is an enlarged view of a portion of FIG. 2, showing details of the disposition of the SCMS device.

Reference is now made to FIG. 3, in which are shown certain details of the disposition of the SCMS device 38 not shown in FIG. 2.

The SCMS device 38 is disposed in the mud-return flow line 14. A first tubular connector 15 connects the SCMS device 38 to a tube 17 which communicates through a second tubular connector 15 with a line 19 conveying a gas sample to a hydrocarbon detector/analyzer 23 having a readout 25. The line 19 is connected to a flow-controller 27, which regulates the flow of an inert carrier gas provided by a cylinder 29 of a compressed inert gas.

The tube 17 and first tubular connector 15 are disposed in a housing 31 which includes a lock-chamber 33 and a ball valve 35. The valve 35 is used to isolate the lock-chamber 33 from the mud-return flow line 14 when the SCMS device 38 is to be removed for maintenance and/or calibration/recalibration.

Figure 4:
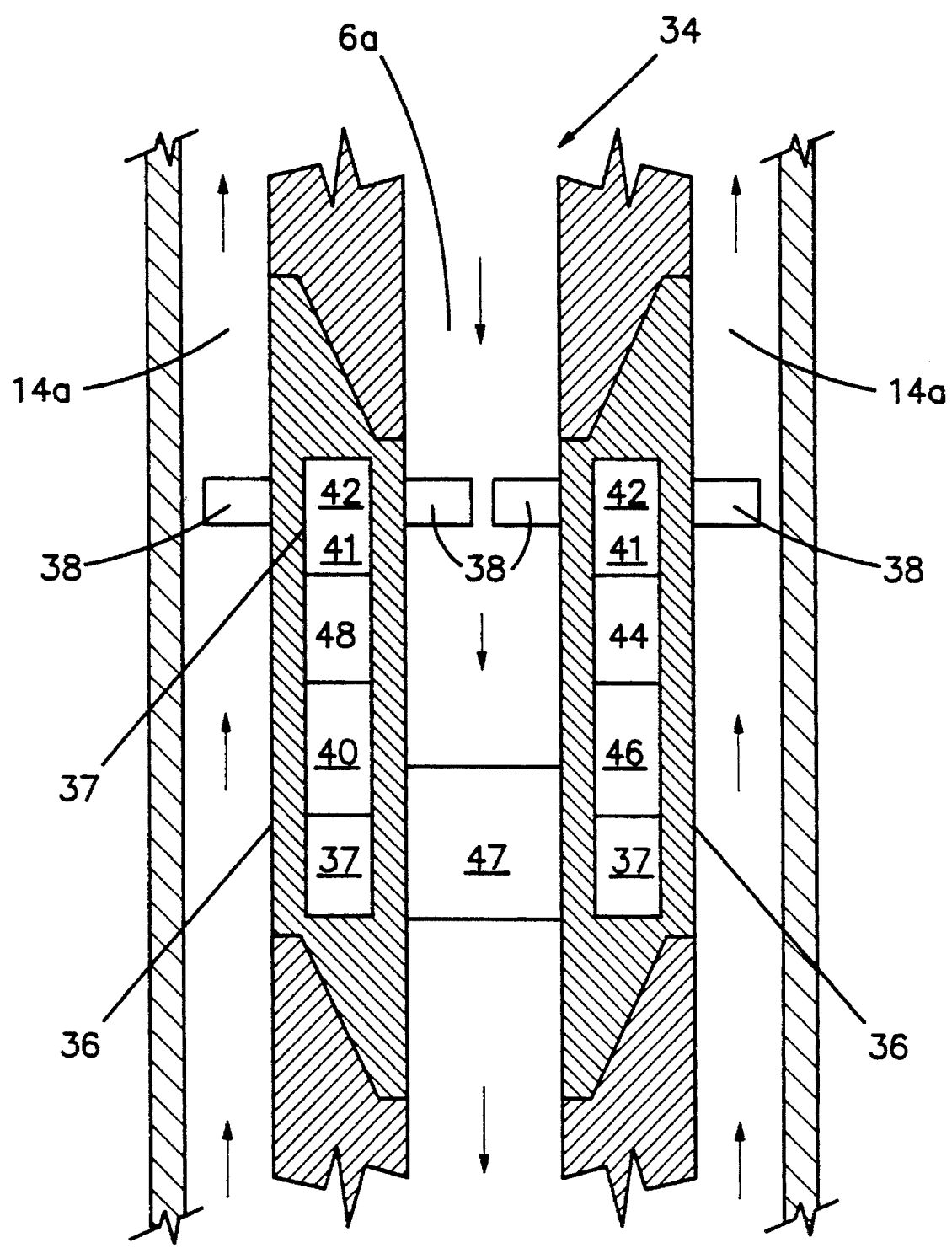
FIG. 4 is a schematic representation of a second embodiment of a method for monitoring oil-drilling mud in accordance with the principles of the present invention.

Reference is now made to FIG. 4, in which is illustrated a second embodiment, Generally designated by the numeral 34, of a method for monitoring oil-drilling mud in accordance with the principles of the present invention.

A first SCMS device 38 is installed below ground in a down-hole drill bore of an oil well near the drill head in contact with returning mud from the drill head in a mud-return flow line 14a. An instrument canister 36 houses a portion of the SCMS device 38, a gas-sensing unit 37, a flow controller 40, an SCMS pressure sensor 42, a down-hole pressure sensor 44, a temperature sensor 48, and electronic hardware 46 programmed to process data from the gas-sensing unit 37, flow controller 40, pressure sensor 42, pressure sensor 44, and temperature sensor 48. A stream of inert gas is passed through the SCMS device 38, and the hydrocarbon-laden gas stream therefrom is input to the gas-sensing unit 37 for identification and quantitative determination of entrained hydrocarbons. The flow controller 40 is used to control the flow of carrier gas through the device 38. All of the auxiliary equipment and instrumentation 36, 37, 40, 42, 44, 46, and 48 is disposed in the well near the SCMS device 38.

Heretofore it has not been possible to monitor the drilling mud directly at the drill site, far below ground, because of the high hydrostatic pressure, and because of high particulate loading of the samples, which would tend to occlude filtration-type sampling devices. The capillary membrane 52 is, however, uniquely suited to perform this function, because the transport mechanism is by permeation rather than diffusion, because the small diameter of the capillary 52 results in extremely high resistance to pressure and abrasion, and because the support member 40 and flights 56 and 62 provide further protection from the hostile environment encountered in the well bore. Should it prove necessary or desirable, the stream of carrier gas could be supplied at a sufficiently high pressure to offset and neutralize the effect of the high external hydrostatic pressure of the oil-mud slurry.

In order to provide a self-contained and self-sufficient unit 34 for monitoring the oil-drilling mud down-hole, the power needed to operate the analytical and electronic hardware is beneficially provided by hydraulic generator vanes 47 disposed in the mud-supply flow stream in the well near the SCMS device 38.

Preferably, the first SCMS device 38 disposed in the well bore at 14a is used in combination with a second SCMS device 38 disposed in the incoming mud-supply stream in a mud-supply flow line 6a. The second SCMS device 38 serves as a reference for any entrained hydrocarbons which may have been carried over by the recycle-mud flow stream.

The preferred embodiments of and best mode of utilizing the present invention will now be illustrated by specific examples of its use in the field.

EXAMPLE I

A first SCMS device 38 shown in FIG. 1 is disposed in the mud-return flow line 14 in which the mud slurry from the borehole 16 is returned past the drill bit 18, drill colar 20, and drill pipe 22, as shown in FIG. 2. A second SCMS device 38 is disposed as a reference device in the standpipe 6 carrying discharge from the pump 8 connected to the suction line 10 leading from the suction pit 12, as shown in FIG. 2. A stream of dry helium gas is passed into the channel 46 and out of the channel 48 of the capillary membrane 52 of each SCMS device 38 to a gas chromatograph (not shown) for identification and quantitative determination of hydrocarbons entrained by the helium.

EXAMPLE II

A first SCMS device 38 shown in FIG. 1 is installed in a down-hole drill bore of an oil well near the drill head in contact with returning mud from the drill head in a mud-return flow line 14a, as shown in FIG. 4. The instrument canister 36 houses a portion of the SCMS device 38, a gas-sensing unit 37, a flow controller 40, an SCMS pressure sensor 42, a down-hole pressure sensor 44, a temperature sensor 48, and electronic hardware 46 programmed to process data input from the gas-sensing unit 37, flow controller 40, pressure sensor 42, pressure sensor 44, and temperature sensor 48. A stream of dry nitrogen is passed through the SCMS device 38 as in Example I, and the hydrocarbon-laden gas stream from the device 38 is input to the gas-sensing unit 37 for identification and quantitative determination of entrained hydrocarbons. The flow controller 40 is used to control the flow of nitrogen to and through the device 38. The power needed to operate the gas-sensing unit 37 and the electronic hardware 46 is provided by hydraulic generator vanes 46 disposed in the mud-return flow stream in the well near the SCMS device 38. The nitrogen to the device 38 is beneficially provided at a pressure approximately equal to and somewhat lower than the hydrostatic pressure in the oil well, in order to reduce the pressure differential on the wall of the capillary membrane 52. It is important that the pressure of the carrier gas be lower than the external hydrostatic pressure, in order to prevent outflow of hydrocarbons vapors through the wall of the capillary membrane 52. A second SCMS device 38 is beneficially disposed in a mud-supply flow line 6a as a reference device for detecting and compensating for any entrained hydrocarbons carried by the recycle-mud flow stream.

EXAMPLE III

The SCMS device 38 shown in FIG. 1 is installed in a down-hole drill bore of an oil well near the drill head in contact with mud returning from the drill head as shown in FIG. 4 at 14a. A stream of dry nitrogen is passed through the SCMS device 38 and into a sample container (not shown), thereby obtaining a sample of the hydrocarbon-laden gas stream.

I claim:

1. A method for monitoring oil-drilling mud, which comprises the steps of:

(a) providing a device comprising a support member, a capillary membrane permeable to hydrocarbons, and flights on the surface of the support member within which the capillary member is supported;

(b) disposing the device in a stream returning mud from a drill hole to the surface of an oil well;

(c) passing a stream of inert gas through the capillary membrane, thereby entraining hydrocarbon vapors in the gas stream; and (d) inputting the gas stream containing the entrained hydrocarbon vapors to an analytical instrument capable of identifying and quantitatively determining the concentrations of the hydrocarbons.

2. The method of claim 1, wherein the device is disposed in the mud-return stream at the surface of the well.

3. The method of claim 1, wherein the device is disposed in the mud-return stream below ground in the well near a drill head.

4. The method of claim 3, further comprising the steps of:

(e) providing a flow controller to control the flow of gas through the device;

(f) disposing the flow controller in the well near the device;

(g) providing a gas-sensing unit for the identification and quantitative determination of the hydrocarbons entrained by the inert gas;

(h) disposing the gas-sensing unit in the well near the device;

(i) providing electronic hardware to process data from the gas-sensing unit and the flow controller;

(j) disposing the electronic hardware in the well near the device;

(k) programming the electronic hardware to process data from the gas-sensing unit and the flow controller;

(l) providing hydraulic generator vanes to provide power for the operation of the gas-sensing unit and the electronic hardware; and (m) disposing the hydraulic generator vanes in the mud-return flow stream in the well near the device.

5. A method for sampling hydrocarbons associated with oil-drilling mud, the method comprising the steps of:

(a) providing a device comprising a support member, a capillary membrane permeable to hydrocarbons, and flights on the surface of the support member within which the capillary member is supported;

(b) disposing the device in a stream returning mud from a drill hole to the surface of an oil well; and (c) passing a stream of inert gas through the capillary membrane, thereby entraining hydrocarbon vapors in the gas stream and obtaining a sample of the hydrocarbons associated with the oil-drilling mud.

6. The method of claim 5, wherein the device is disposed in the mud-return stream at the surface of the well.

7. The method of claim 5, wherein the device is disposed in the mud-return stream below ground in the well near a drill head.

* * * * *